United States Patent
Dai et al.

(10) Patent No.: US 9,284,257 B2
(45) Date of Patent: Mar. 15, 2016

(54) SEPARATION METHOD FOR DINITROTOLUENE AND MIXED ACID IN A TOLUENE TO DINITROTOLUENE PROCESS

(71) Applicants: BASF SE, Ludwigshafen (DE); SHANGHAI BASF POLYURETHANE COMPANY LIMITED, Shanghai (CN)

(72) Inventors: Yuanshen Dai, Mannheim (DE); Da Peng Li, Shanghai Fengxian (CN); Pei Shi Jia, Shanghai Fengxian (CN); Zhan Cai, Shanghai (CN); Samuel Neto, Mannheim (DE)

(73) Assignees: BASF SE, Ludwigshafen (DE); Shanghai BASF Polyurethane Company Limited, Shanghai (CN)

( * ) Notice: Subject to any disclaimer, the term of this patent is extended or adjusted under 35 U.S.C. 154(b) by 0 days.

(21) Appl. No.: 14/653,687

(22) PCT Filed: Dec. 10, 2013

(86) PCT No.: PCT/EP2013/076002
§ 371 (c)(1),
(2) Date: Jun. 18, 2015

(87) PCT Pub. No.: WO2014/095469
PCT Pub. Date: Jun. 26, 2014

(65) Prior Publication Data
US 2015/0329469 A1    Nov. 19, 2015

(30) Foreign Application Priority Data
Dec. 20, 2012    (WO) ............... PCT/CN2012/086999

(51) Int. Cl.
C07C 205/00    (2006.01)
C07C 201/08    (2006.01)

(52) U.S. Cl.
CPC .................... *C07C 201/08* (2013.01)

(58) Field of Classification Search
CPC .... C07C 201/08; C07C 201/14; C07C 205/06
USPC ........................................................ 568/934
See application file for complete search history.

(56) References Cited

U.S. PATENT DOCUMENTS 7,851,661 B2    12/2010 Buettner et al.
8,697,921 B2    4/2014 Deckert et al.
8,895,783 B2    11/2014 Raichle et al.
2013/0041188 A1    2/2013 Leschinski et al.
2014/0039227 A1    2/2014 Neto et al.
2014/0107378 A1    4/2014 Vandewalle et al.

OTHER PUBLICATIONS

International Search Report Issued Feb. 18, 2014 in PCT/EP13/076002 Filed Dec. 10, 2013.

*Primary Examiner* — Jafar Parsa
(74) *Attorney, Agent, or Firm* — Oblon, McClelland, Maier & Neustadt, L.L.P.

(57) ABSTRACT

Proposed is a separation method in a toluene to dinitrotoluene process, wherein said method with a first process step comprising feeding a toluene comprising first stream (1) and a nitric acid comprising second stream (2) into a first reactor (R1), reacting of the toluene comprising first stream (1) and the nitric acid comprising second stream (2) within the first reactor (R1) to a first reaction mixture (3), said first reaction mixture (3) comprising a first liquid/liquid mixed phase of an acid phase and an organic phase comprising mononitrotoluene, feeding the first reaction mixture (3) into a first separation device (S1), separating the first reaction mixture (3) within the first separation device (S1) into a first forward stream (4) having a flow direction to a second process step and a first backward stream (5) having a flow direction back to the first reactor (R1), said method having a second process step comprising feeding the first forward stream (4) into a second reactor (R2), feeding a nitric acid comprising third stream (6) and a sulfuric acid comprising fourth stream (7) into the second reactor (R2), reacting of the first forward stream (4), the nitric acid comprising third stream (6) and the sulfuric acid comprising fourth stream (7) within the second reactor (R2) to a second reaction mixture (8), said second reaction mixture (8) comprising a second liquid/liquid mixed acid phase and an organic phase comprising mononitrotoluene and dinitrotoluene, feeding the second reaction mixture (8) into a second separation device (S2), separating the second reaction mixture (8) within the second separation device (S2) into a second forward stream (9) having a flow direction to a process output and a second backward stream (10) having a flow direction back to the first reactor (R1), wherein fine separating of at least one of the streams (4, 5, 9, 10) after the first separation step (S1) and/or the second separation step (S2) in a coalescer is carried out.

15 Claims, 6 Drawing Sheets

Figure 1:
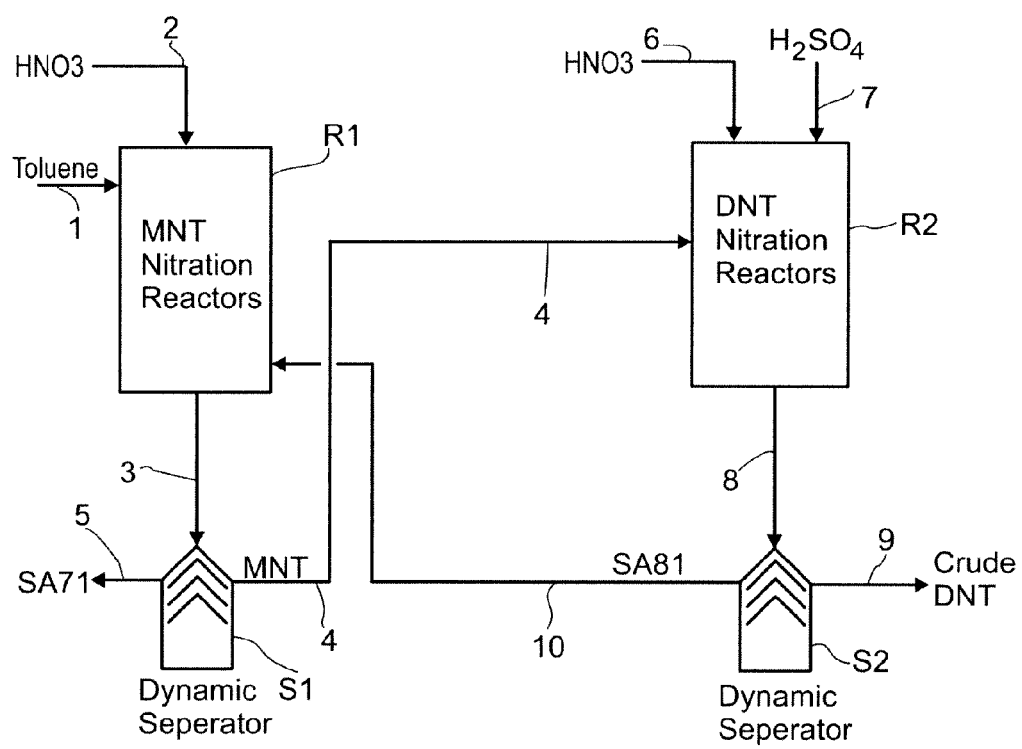

SEPARATION METHOD FOR DINITROTOLUENE AND MIXED ACID IN A TOLUENE TO DINITROTOLUENE PROCESS

The invention relates to a separation method in a toluene to dinitrotoluene process by separating an organic phase from a mixed acid phase by the use of a coalescer.

The organic phase comprises mono- and/or dinitrotoluene. The mixed acid phase comprises sulfuric acid, nitric acid, nitrous acid and nitrogene oxides gas e.g. resulting from the decomposition of nitrous acid.

The nitration of toluene to dinitrotoluene is well known. In general a toluene to dinitrotoluene process consists of two steps. In a first step toluene reacts with nitric acid in a nitration reactor to mononitrotoluene as an organic phase and in a second step the mononitrotoluene reacts with nitric acid and sulfuric acid in a nitration reactor to dinitrotoluene as an organic phase.

The effluent of each of the reactors is a mixture of an organic phase and a mixed acid phase. In order to obtain a high concentration of an organic phase the organic phase can be separated from the acid phase. Several methods to separate the organic phase from the acid phase of the effluent of reactors exist.

A dynamic separator is used in U.S. Pat. No. 7,851,661B2 for the separation of a reaction product into an organic phase comprising mononitrotoluene and an aqueous phase comprising sulfuric acid. The dynamic separation occurs by centrifugal force or static settlement separation by gravity.

A problem of dynamic separation is that dynamic separators cannot completely separate organics phase from mixed acid phase due to limitation in the technical structure by which a separator is equipped. The limitation of dynamic separator technical structure is that two phases interphase is controlled in the equipment by so-called regular rings which function similar to a wear in a static settler at heavy and light phases discharger sides, and the regular ring is a kind of fixed device in the equipment which can not be controlled during normal operation. The only way of adjustment of the equipment is to shut down and disassemble the dynamic separator and change the regular rings into a rings of different dimensions. A shut down of the dynamic separator decreases the efficiency of the separation process.

Also during operation, as concentration, the density of both phases in reactor products is always changing from time to time and having a fixed separator e.g. with a wear provided, the entrainments is always possible to happen in both phases.

The disadvantages of such entrainments are an increase of internal circulation in a nitration system thereby also reducing the reaction residence time in a reactor and a possible change of the two phases ratio in reactors. Also, potential safety risks exist in case the concentration of certain reactor products increases above a critical level. One example for a potential risk of explosion is if the toluene concentration within a mononitrotoluene reactor is increasing above a certain level resulting in by-products such as black acid. A reaction possibility for the by-product of black acid components can be shown as follows:

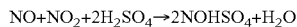

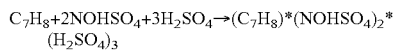

Having black complex component provided a potential decomposition risk exists.

The black acid component can occur when residence times in a mononitrotoluene reactor is too short or in case there is a lack of nitric acid. An advantage of the present invention is a reduction of the internal circulation of about 10% which results in a reduction of residence time in the mononitrotoluene reactor of about 10%. The benefits are less safety risks and an improved and efficient control of the toluene concentration. By this the bottleneck of the production plant operation is removed.

In U.S. Pat. No. 5,902,910A a reaction product is separated into an organic phase containing mononitrotoluene and a first spent acid phase by a phase separator. Also in U.S. Pat. No. 5,902,910A an organic phase containing dinitrotoluene is separated from a second spent acid phase by a phase separator.

In the U.S. Pat. No. 6,506,948B1 a phase separator is mentioned after certain stages of production but no more details regarding the kind of separator and/or the basic principle of the separation method and/or the separation process are given.

A general disadvantage of phase separators is plugging which often occurs after a certain operation time. Reasons for plugging can be that corroded particles get stuck in devices and/or fouling products block the devices. As a result of plugging the production process has to be shutdown and phase separators to be disassembled and cleaned. A shut down of a separator decreases the efficiency of the separation process.

Therefore it is the objective problem of the invention to provide an improved separation method with an increased separation efficiency and which needs less residence time for separation and overcomes the aforementioned disadvantages.

The objective problem is solved by a separation method in a toluene to dinitrotoluene process, said method with a first process step comprising feeding a toluene comprising first stream and a nitric acid comprising second stream into a first reactor, reacting of the toluene comprising first stream and the nitric acid comprising second stream within the first reactor to a first reaction mixture, said first reaction mixture comprising a first liquid/liquid mixed phase of an acid phase and an organic phase comprising mononitrotoluene, feeding the first reaction mixture into a first separation device, separating the first reaction mixture within the first separation device into a first forward stream having a flow direction to a second process step and a first backward stream having a flow direction back to the first reactor, said method having a second process step comprising feeding the first forward stream into a second reactor, feeding a nitric acid comprising third stream and a sulfuric acid comprising fourth stream into the second reactor, reacting of the first forward stream, the nitric acid comprising third stream and the sulfuric acid comprising fourth stream within the second reactor to a second reaction mixture, said second reaction mixture comprising a second liquid/liquid mixed acid phase and an organic phase comprising mononitrotoluene and dinitrotoluene, feeding the second reaction mixture into a second separation device, separating the second reaction mixture within the second separation device into a second forward stream having a flow direction to a process output and a second backward stream having a flow direction back to the first reactor, wherein fine separating of at least one of the streams after the first separation step and/or the second separation step in a coalescer is carried out.

Under a reactor according to the present invention a device for containing and controlling a chemical reaction is understood.

Under a separation device according to the present invention a device for the separation of different substances is understood. A separation device according to the present invention preferably is a centrifugal separator.

Under a forward stream according to the present invention a stream with a downstream direction in a process, preferably a stream to a further process step, a stream to a process output is understood.

Under a backward stream according to the present invention a stream with an upstream direction in a process, preferably a stream to a previous process step, a stream to a process input is understood.

Under a process output according to the present invention an output of a product of a final process step, preferably the output of the product dinitrotoluene is understood.

Under fine separating according to the present invention a separation of a liquid/liquid mixed acid phase from an organic phase and a separation of a gas phase is understood. The mixed acid phase preferably comprises sulfuric acid, nitric acid and nitrous acid. The organic phase preferably comprises dinitrotoluene and/or mononitrotoluene. The gas phase preferably comprises nitrogene oxides.

Under a first separation step according to the present invention a separation step which is upstream of a second separation step is understood. Preferably in the first separation step a process stream is separated by a dynamic separator.

Under a second separation step according to the present invention a separation step which is downstream of a first separation step is understood. Preferably in the second separation step a process stream is separated by a static separator. An advantage of a static separator in the second separation step is that the residence time can be reduced which increases the throughput in a process.

Under a coalescer according to the present invention a static separator is understood. The static separation is based on a static settlement and/or on internals of the separator for separation of phases. Preferably internals are mesh types, wire types, fiber candles, vane packs and/or other structures inside the separator separating the phases. In case of only static settlement also devices without internals can be used.

Preferably the coalescer is a mechanical and/or an electrostatic coalescer. Mechanical coalescers use filters and/or internals like baffles while electrostatic coalescers use direct current (DC) or alternating current (AC) electric fields or combinations thereof.

Preferably the coalescer separates a mixed acid phase from an organic phase of a liquid/liquid phase and also separates a gas phase.

In case a phase is corrosive a preferred material for of least the elements of a separator which are in contact with the corrosive phase is polytetrafluorethylene (PTFE).

Examples of preferred coalescers and/or internals are of the vendors Franken and/or Pall, more preferred is the internal Pall type LCS4H2HH. The preferred pore sizes of internal fiber webs can be in the range of about 10 to 20 micron. For the separation of a gas phase the installation of a gas bag is preferred.

A separation method wherein fine separating the second backward stream having a flow direction back to the first reactor in a coalescer is carried out.

A separation method wherein fine separating the second forward stream having a flow direction to the process output in a coalescer is carried out.

A separation method wherein fine separating the first forward stream having a flow direction to the second process step in a coalescer is carried out.

A separation method wherein fine separating the first backward stream having a flow direction back to the first reactor in a coalescer is carried out.

A separation method wherein the second backward stream having a flow direction back to the first reactor comprises a liquid/liquid mixed acid phase comprising sulfuric acid concentration in the range from about 70 wt % to about 95 wt %, preferably from about 75 wt % to about 85 wt %, more preferably from about 78 wt % to about 79 wt % and nitric acid in the range from about 0.1 wt % to about 5 wt %, preferably from about 0.2 wt % to about 3 wt %, more preferably from about 0.5 wt % to about 1.5 wt %, and mononitrotoluene and dinitrotoluene as an organic phase and combinations thereof.

A separation method wherein fine separating the second forward stream having a flow direction to the process output comprises a liquid/liquid mixed acid phase comprising sulfuric acid in the range from about 0.1 wt % to about 20 wt %, preferably from about 0.2 wt % to about 15 wt %, more preferably from about 0.3 wt % to about 10 wt % and nitric acid in the range from about 0.1 wt % to about 10 wt %, preferably from about 0.2 wt % to about 5 wt %, more preferably from about 0.3 wt % to about 3 wt %, and mononitrotoluene and dinitrotoluene as an organic phase and combinations thereof.

A separation method wherein fine separating the first forward stream having a flow direction to a second process step comprises a liquid/liquid mixed acid phase comprising sulfuric acid in the range from about 0.1 wt % to about 20 wt %, preferably from about 0.2 wt % to about 15 wt %, more preferably from about 0.3 wt % to about 10 wt % and nitric acid in the range from about 0.1 wt % to about 15 wt %, preferably from about 0.2 wt % to about 5 wt %, more preferably from about 0.3 wt % to about 1.5 wt %, and mononitrotoluene and dinitrotoluene as an organic phase and combinations thereof.

A separation method wherein fine separating the first backward stream having a flow direction back to the first reactor comprises a liquid/liquid mixed acid phase comprising sulfuric acid in the range from about 60 wt % to about 80 wt %, preferably from about 65 wt % to about 75 wt %, more preferably from about 69 to about 72 wt % and nitric acid in the range from about 0.1 wt % to about 5 wt %, preferably from about 0.2 wt % to about 3 wt %, more preferably from about 0.3 wt % to about 1.5 wt %, and mononitrotoluene and dinitrotoluene as an organic phase and combinations thereof.

A separation method wherein the toluene concentration in the first reactor is in the range from about 0 wt % to about 10 wt %, preferably from about 0.1 wt % to about 7 wt %, more preferably from about 0.2 wt % to about 5 wt %.

A separation method wherein the coalescer is a predominantly cylindrical device having a longitudinal axis, this longitudinal axis differing from a horizontal line with a gradient in the range from 0.2° to about 5°, more preferably from about 0.5° to about 2°.

A separation method wherein at least one of the streams feeding the coalescer has a dynamic viscosity in the range from about 0.1 mPas to about 20 mPas, preferably from about 0.2 mPas to about 15 mPas, more preferably from about 1 mPas to about 7 mPas.

A separation method wherein at least one of the streams feeding the coalescer has a interfacial tension in the range from about 0.5 mN/m to about 95 mN/m, preferably from about 10 mN/m to about 90 mN/m, more preferably from about 40 mN/m to about 80 mN/m.

For determination of the interfacial tension according to the present invention the standard Du Noüy ring method is used.

A separation method wherein at least one of the streams feeding the coalescer has a flow rate per surface area through the coalsecer in the range from about 2 m$^3$/h/m$^2$ to about 10 m³/h/m², preferably from about 3 m³/h/m² to about 8 m³/h/m², more preferably from about 4 m³/h/m² to about 6 m³/h/m².

A separation method wherein at least one of the streams feeding the coalescer has a residence time in the coalsecer in the range from about 1 min to about 30 min, preferably from about 2 min to about 10 min, more preferably from about 3 min to about 6 min.

Under residence time according to the present invention is understood the time starting when a feed enters the coalescer to the time this feed exits the coalescer.

The invention is explained below with reference to figures and tables.

Figure 2:
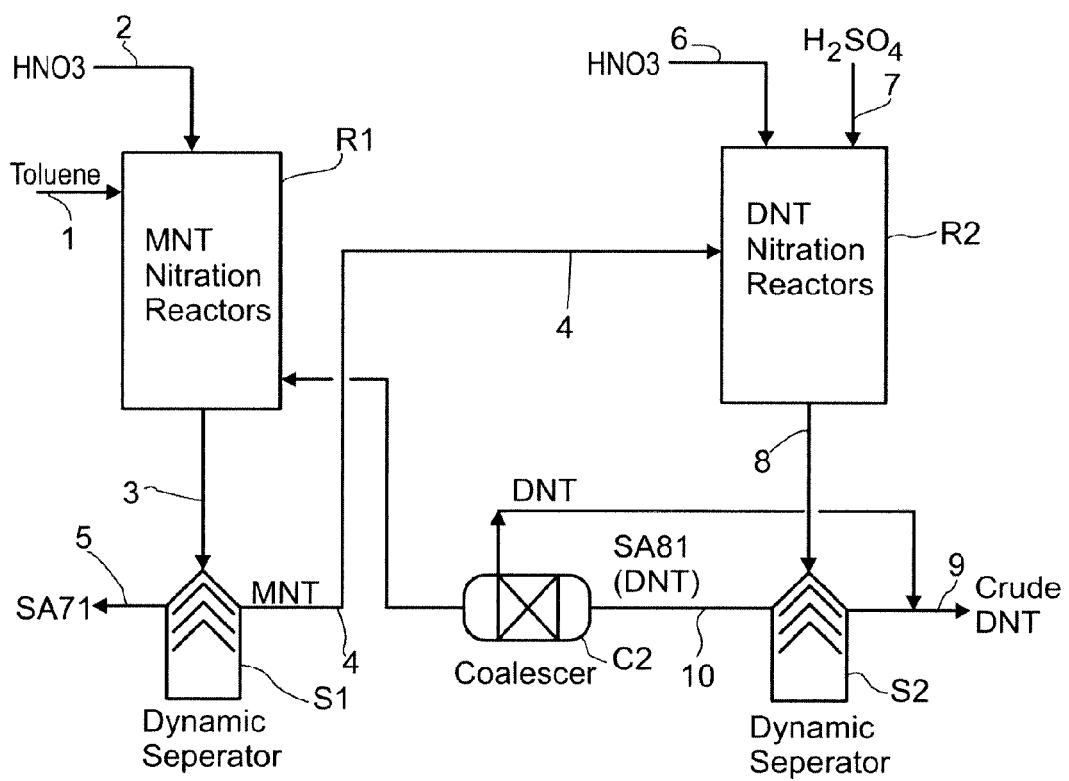
Figure 3:
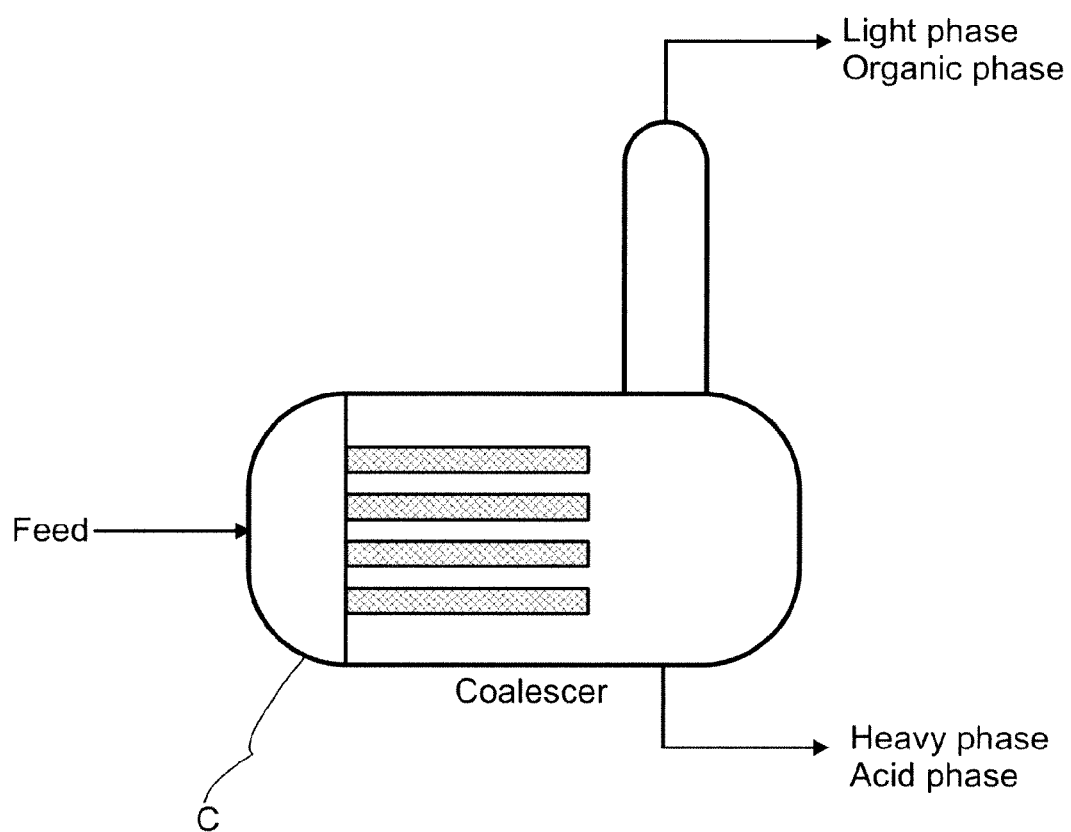
Figure 4:
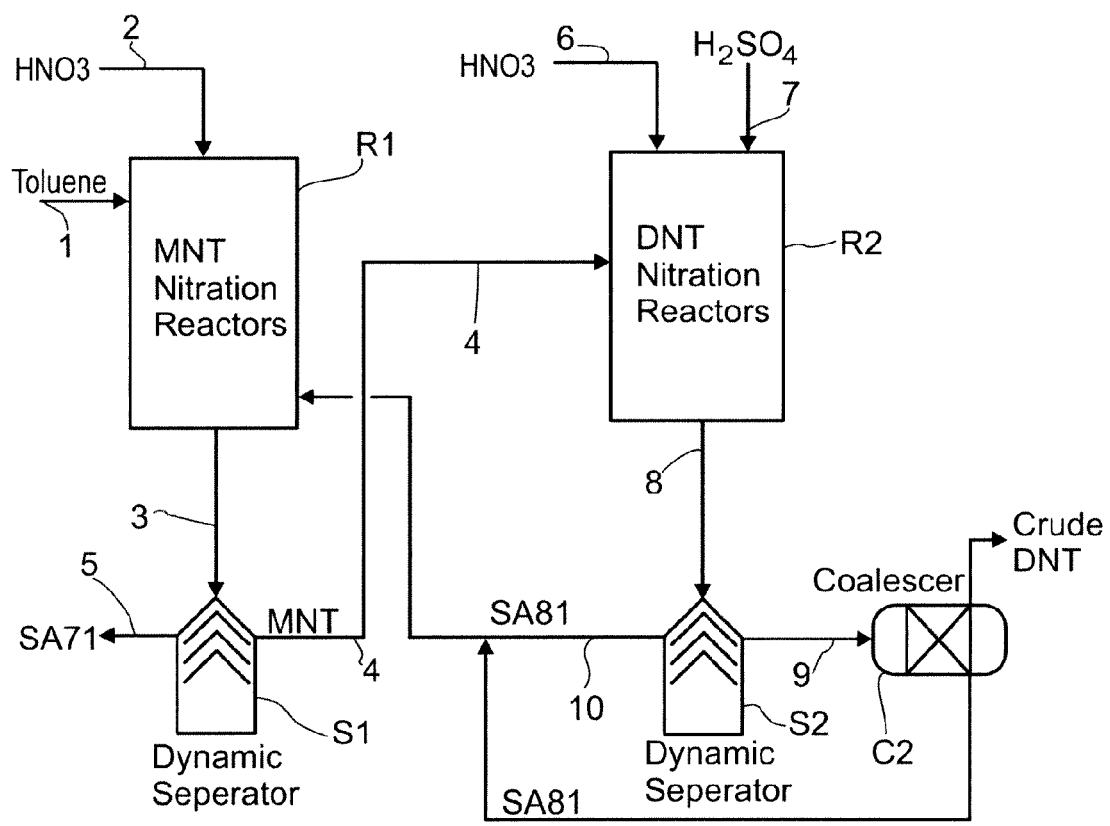
Figure 5:
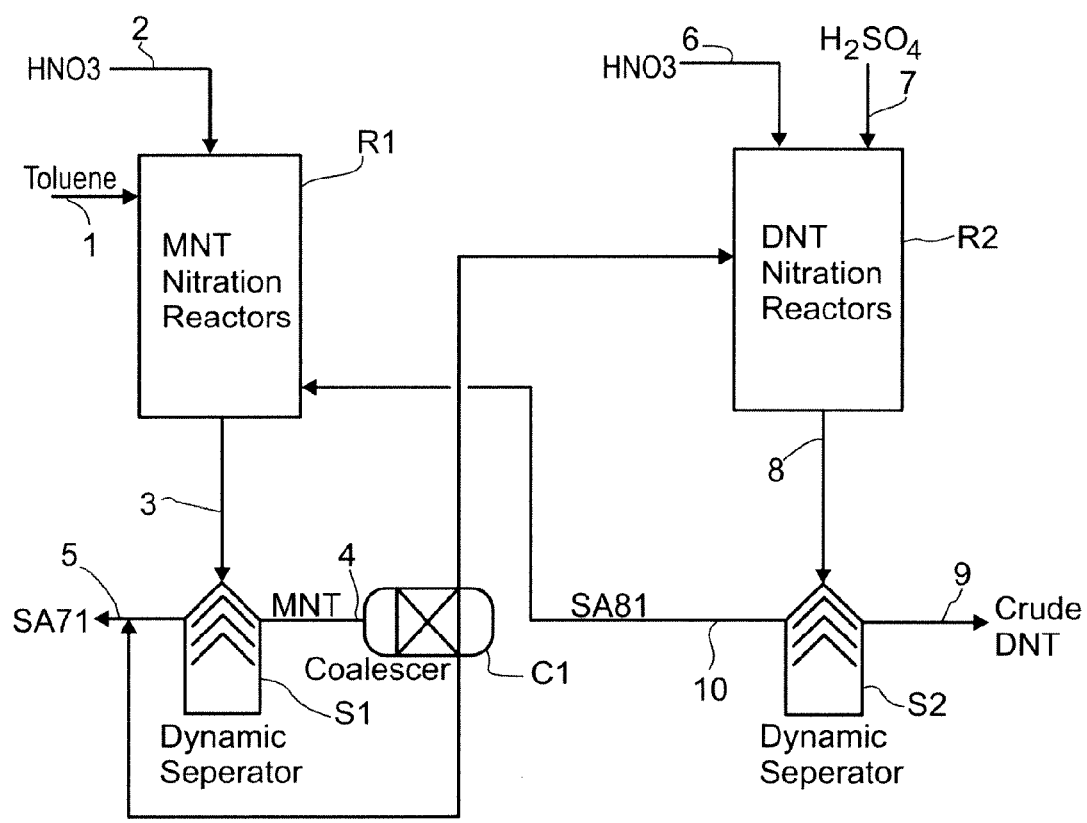
Figure 6:
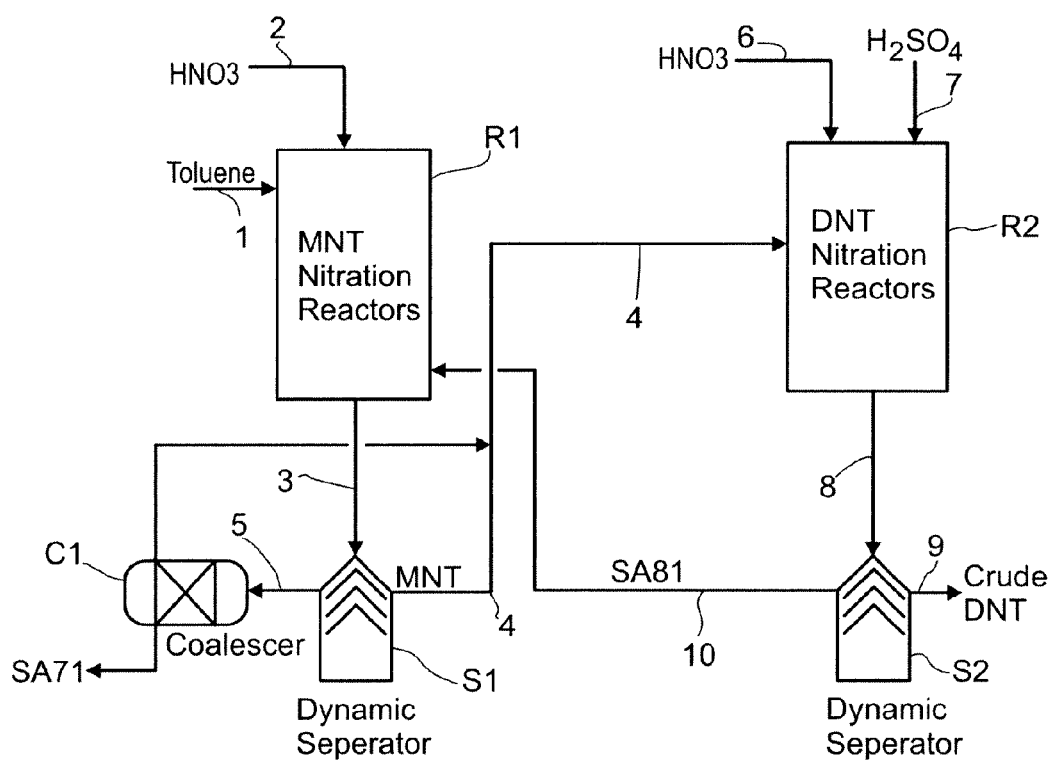

The figures show in detail:

FIG. 1: a schematic overview of an original toluene nitration to dinitrotoluene process, FIG. 2: a schematic overview of the toluene nitration to dinitrotoluene process with a coalescer installed after the dynamic separator of the DNT nitration reactor in the backward stream to the MNT nitration reactor, FIG. 3: a schematic overview of a coalescer, FIG. 4: a schematic overview of the toluene nitration to dinitrotoluene process with a coalescer installed after the dynamic separator of the DNT nitration reactor in direction of the flow output stream, FIG. 5: a schematic overview of the toluene nitration to dinitrotoluene process with a coalescer installed after the dynamic separator of the MNT nitration reactor in the flow output stream to the DNT nitration reactor, FIG. 6: a schematic overview of the toluene nitration to dinitrotoluene process with a coalescer installed after the dynamic separator of the MNT nitration reactor in the backward stream.

The identical reference characters in the figures stand for the same or corresponding features. FIG. 1 shows a schematic overview of an original toluene nitration to dinitrotoluene process. In the toluene nitration to dinitrotoluene process, normally the nitration is carried out in two steps. The first step is a mononitrotoluene nitration and the second step is a dinitrotoluene nitration. The first process step is feeding a toluene comprising first stream 1 and a nitric acid comprising second stream 2 into a first reactor R1. In the first reactor R1 the first stream 1 and the second stream 2 are reacting to a first reaction mixture 3. The first reaction mixture 3 comprises a first liquid/liquid mixed phase of an organic phase comprising of mononitrotoluene and dinitrotoluene and an acid phase. Both phases are mutual dissolved. As an example the liquid/liquid mixed acid phase of the first reaction mixture 3 comprises sulfuric acid in the range from about 70 wt % to about 71 wt %, nitric acid in the range from about 0.1 wt % to about 1 wt %, nitrous acid in the range from about 0.4 wt % to about 1.5 wt % and a certain amount of Nitrogene oxides gas resulting from the decomposition of nitrous acid. The first reaction mixture 3 is fed into a first separation device S1, which is a dynamic separator. The first separation device S1 is separating the reaction mixture 3 into a first forward stream 4 having a flow direction to the second process step and a first backward stream 5 having a flow direction back to the first reactor R1. The first forward stream 4 should comprise of as much organic phase like mononitrotoluene as possible and the first backward stream 5 should cycle the acid phase back to the first reactor R1. The second process step is feeding the first forward stream 4, a nitric acid comprising third stream 6 and a sulfuric acid comprising fourth stream 7 into a second reactor R2. In the second reactor R2 the first forward stream 4, the nitric acid comprising third stream 6 and the sulfuric acid comprising fourth stream 7 are reacting to a second reaction mixture 8. The second reaction mixture 8 comprises a first liquid/liquid mixed phase of an organic phase comprising of mononitrotoluene and dinitrotoluene and an acid phase. Both phases are mutual dissolved. As an example the liquid/liquid mixed acid phase of the second reaction mixture 8 comprises sulfuric acid in the range from about 78 wt % to about 79 wt %, nitric acid in the range from about 0.5 wt % to about 1.5 wt %, nitrous acid in the range from about 0.8 wt % to about 1.5 wt % and a certain amount of Nitrogene oxides gas resulting from the decomposition of nitrous acid. The second reaction mixture 8 is fed into a second separation device S2, which is a dynamic separator. The second separation device S2 is separating the second reaction mixture 8 into a second forward stream 9 having a flow direction to process output and a second backward stream 10 having a flow direction back to the first reactor R1. The second forward stream 9 should comprise of as much organic phase like crude dinitrotoluene as possible and the second backward stream 10 should cycle the acid phase back to the first reactor R1.

FIG. 2 shows a schematic overview of the original toluene nitration to dinitrotoluene process of FIG. 1 with the difference that in the second process step a coalsecer C2 is installed. The coalescer C2 is fine separating the second backward stream 10. By the fine separation as much organic phase like crude dinitrotoluene as possible should access the second forward stream 9 having a flow direction to process output and as much acid phase as possible should be cycled back to the first reactor R1.

FIG. 3 shows a schematic overview of a coalescer C. The coalescer C is fed by a stream which is fine separated into an organic phase and an acid phase. In common the organic phase is a light phase compared to the acid phase as a heavy phase. The coalescer C is a predominantly cylindrical device having a horizontal axis, this horizontal axis differing from a horizontal line with a gradient. This gradient improves the removal of gas along the gradient and out of the coalsecer C.

FIG. 4 shows a schematic overview of the original toluene nitration to dinitrotoluene process of FIG. 1 with the difference that in the second process step a coalsecer C2 is installed. The coalescer C2 is fine separating the second forward stream 9. By the fine separation as much organic phase like crude dinitrotoluene as possible should access process output and as much acid phase as possible should be cycled back to the first reactor R1 in the second backward stream 10.

FIG. 5 shows a schematic overview of the original toluene nitration to dinitrotoluene process of FIG. 1 with the difference that in the first process step a coalsecer C1 is installed. The coalescer C1 is fine separating the first forward stream 4. By the fine separation as much organic phase comprising mononitrotoluene as possible should access the second reactor R2 and as much acid phase as possible should be cycled back to the first reactor R1 in the first backward stream 5.

FIG. 6 shows a schematic overview of the original toluene nitration to dinitroluene process of FIG. 1 with the difference that in the first process step a coalsecer C1 is installed. The coalescer C1 is fine separating the first backward stream 5. By the fine separation as much organic phase comprising mononitrotoluene as possible should access the second reactor R2 and as much acid phase as possible should be cycled back to the first reactor R1 in the first backward stream 5.

The following tables 1 to 3 show production data as examples according to the coalescer C as described in FIG. 3. The tables differ regarding to the residence times of 1, 3 and 5 minutes in the coalscer, which results in different feed rates and/or loads for coalesce during plant trials. The residence times can also be defined as a percentage of coalesced rates/or loads.

TABLE 1

Experimental data of plant trials with the resident time of 1 minute in the coalscer.

| Coalescer residence time 1 mins | 1 FEED inlet | 2 light phase outlet | 3 heavy phase outlet |
|---|---|---|---|
| Mass Frac | | | |
| DNT[a] (MNT, toluene) | 14.6 wt % | 91.2 wt % | 7.9 wt % |
| HNO3 | 0.8 wt % | 3.1 wt % | 0.6 wt % |
| H2SO4 | 71.7 wt % | 0.8 wt % | 77.6 wt % |
| HNO2 (NOx) | 1-1.5 wt % | 1.5-2 wt % | 1.0-1.5 wt % |
| H2O | 11.5 wt % | 0.6 wt % | 12.9 wt % |
| CRESOL[b] | 50-200 ppm | 50-200 ppm | 50-200 ppm |
| other organics/acids/inerts[c] | 0.1-0.2 wt % | 0.1-2 wt % | 0.01-0.2 wt % |
| Temperature C. | 65 | 65 | 65 |
| Density kg/cum | 1551 | 1337 | 1556 |

[a]DNT containing tracing MNT and toluene
[b]Cresol including isomers of nitrocresol, dinitrocresol, trinitrocresol,
[c]other organics/acids/inerts including acetic acid, formic acid, oxalic acid, HCN, CO, CO2 etc.

TABLE 2

Experimental data of plant trials with the resident time of 3 minutes in the coalscer.

| Coalescer residence time 3 mins | 1 FEED inlet | 2 light phase outlet | 3 heavy phase outlet |
|---|---|---|---|
| Mass Frac | | | |
| DNT[a] (MNT, toluene) | 14.6 wt % | 93.0 wt % | 4.9 wt % |
| HNO3 | 0.8 wt % | 2.1 wt % | 0.6 wt % |
| H2SO4 | 71.7 wt % | 0.6 wt % | 80.1 wt % |
| HNO2 (NOx) | 1-1.5 wt % | 1.5-2 wt % | 1-1.5 wt % |
| H2O | 11.5 wt % | 0.6 wt % | 13.3 wt % |
| CRESOL[b] | 50-200 ppm | 50-200 ppm | 50-200 ppm |
| other organics/acids/inerts[c] | 0.1-0.2 wt % | 0.1-2 wt % | 0.01-0.2 wt % |
| Temperature C. | 65 | 65 | 65 |
| Density kg/cum | 1550 | 1334 | 1558 |

[a]DNT containing tracing MNT and toluene
[b]Cresol including isomers of nitrocresol, dinitrocresol, trinitrocresol,
[c]other organics/acids/inerts including acetic acid, formic acid, oxalic acid, HCN, CO, CO2 etc

The invention claimed is:

1. A separation method in a toluene to dinitrotoluene process, said method comprising:
   i) feeding a toluene comprising first stream (1) and a nitric acid comprising second stream (2) into a first reactor (R1),
   ii) reacting the toluene comprising first stream (1) with the nitric acid comprising second stream (2) within the first reactor (R1) to obtain a first reaction mixture (3), which comprises a first liquid/liquid mixed phase of an acid phase and an organic phase comprising mononitrotoluene,
   iii) feeding the first reaction mixture (3) into a first separation device (S1),
   iv) separating the first reaction mixture (3) within the first separation device (S1) into a first forward stream (4) and a first backward stream (5) flowing back to the first reactor (R1),
   v) feeding the first forward stream (4) into a second reactor (R2),
   vi) feeding a nitric acid comprising third stream (6) and a sulfuric acid comprising fourth stream (7) into the second reactor (R2),
   vii) reacting the first forward stream (4), the nitric acid comprising third stream (6) and the sulfuric acid comprising fourth stream (7) within the second reactor (R2) to a second reaction mixture (8), which comprises a second liquid/liquid mixed acid phase and an organic phase comprising mononitrotoluene and dinitrotoluene,
   viii) feeding the second reaction mixture (8) into a second separation device (S2), and
   ix) separating the second reaction mixture (8) within the second separation device (S2) into a second forward stream (9) flowing to a process output and a second backward stream (10) flowing back to the first reactor (R1),
   wherein
   a fine separation of at least one of the streams (4, 5, 9, 10) after said separating iv) and/or after said separating ix) is carried out in a coalescer.

2. The separation method of claim 1, wherein a fine separation of the second backward stream (10) is carried out in a coalescer.

3. The separation method of claim 1, wherein a fine separation of the second forward stream (9) is carried out in a coalescer.

4. The separation of claim 1, wherein a fine separation of the first forward stream (4) is carried out in a coalescer.

5. The separation method of claim 1, wherein a fine separation of the first backward stream (5) is carried out in a coalescer.

6. The separation method of claim 1, wherein the second backward stream (10) comprises a liquid/liquid mixed acid phase comprising sulfuric acid of from about 70 wt % to about 95 wt % and nitric acid of from about 0.1 wt % to about 5 wt %, and an organic phase comprising mononitrotoluene and dinitrotoluene.

7. The separation method of claim 1, wherein a fine separation of the second forward stream (9) comprises a liquid/liquid mixed acid phase comprising sulfuric acid of from about 0.1 wt % to about 20 wt % and nitric acid of from about 0.1 wt % to about 10 wt %, and an organic phase comprising mononitrotoluene and dinitrotoluene.

8. The separation of claim 1, wherein a fine separation of the first forward stream (4) comprises a liquid/liquid mixed acid phase comprising sulfuric acid of from about 0.1 wt % to about 20 wt % and nitric acid of from about 0.1 wt % to about 15 wt %, and an organic phase comprising mononitrotoluene and dinitrotoluene.

9. The separation method of claim 1, wherein a fine separation of the first backward stream (5) comprises a liquid/liquid mixed acid phase comprising sulfuric acid of from about 60 wt % to about 80 wt % and nitric acid of from about 0.1 wt % to about 5 wt %, and an organic phase comprising mononitrotoluene and dinitrotoluene.

10. The separation method of claim 1, wherein a toluene concentration in the first reactor (R1) ranges from about 0 wt % to about 10 wt %.

11. The separation method of claim 1, wherein the coalescer is a predominantly cylindrical device having a longitudinal axis, which differs from a horizontal line with a gradient ranging from about 0.2° to about 5°.

12. The separation method of claim 1, wherein at least one of the streams (4, 5, 9, 10) feeding the coalescer has a dynamic viscosity ranging from about 0.1 mPas to about 20 mPas.

13. The separation method of claim 1, wherein at least one of the streams (4, 5, 9, 10) feeding the coalescer has a interfacial tension ranging from about 40 mN/m to about 80 mN/m.

14. The separation method of claim 1, wherein at least one of the streams (4, 5, 9, 10) feeding the coalescer has a flow rate per surface area through the coalsecer ranging from about 2 $m^3/h/m^2$ to about 10 $m^3/h/m^2$.

15. The separation method of claim 1, wherein at least one of the streams (4, 5, 9, 10) feeding the coalescer has a residence time in the coalsecer ranging from about 1 min to about 30 min.

\* \* \* \* \*